(12) United States Patent
Bunce

(10) Patent No.: US 7,578,177 B2
(45) Date of Patent: Aug. 25, 2009

(54) MEMS EMISSIONS SENSOR SYSTEM FOR A TURBINE ENGINE

(75) Inventor: Richard H. Bunce, Altamonte Springs, FL (US)

(73) Assignee: Siemens Energy, Inc., Orlando, FL (US)

( * ) Notice: Subject to any disclaimer, the term of this patent is extended or adjusted under 35 U.S.C. 154(b) by 115 days.

(21) Appl. No.: 11/804,436

(22) Filed: May 18, 2007

(65) Prior Publication Data

US 2008/0282770 A1 Nov. 20, 2008

(51) Int. Cl.
*G01M 15/00* (2006.01)
(52) U.S. Cl. .................................. 73/112.01
(58) Field of Classification Search ............. 73/112.01, 73/112.03, 112.04, 112.05, 112.06
See application file for complete search history.

(56) References Cited

U.S. PATENT DOCUMENTS

| | | | |
|---|---|---|---|
| 5,469,369 A | 11/1995 | Rose-Pehrsson et al. | |
| 5,988,522 A | 11/1999 | Glezer et al. | |
| 5,994,638 A | 11/1999 | Edelson | |
| 6,029,442 A | 2/2000 | Caren et al. | |
| 6,047,543 A | 4/2000 | Caren et al. | |
| 6,076,392 A | 6/2000 | Drzewiecki | |
| 6,321,531 B1 | 11/2001 | Caren et al. | |
| 6,338,820 B1 | 1/2002 | Hubbard et al. | |
| 6,823,736 B1 | 11/2004 | Brock et al. | |
| 7,151,260 B2 * | 12/2006 | Markham et al. | 250/339.08 |
| 2002/0016665 A1 | 2/2002 | Ulyanov et al. | |
| 2003/0020062 A1 | 1/2003 | Faris | |
| 2003/0039693 A1 | 2/2003 | Sandhage | |
| 2003/0230415 A1 | 12/2003 | Wilson et al. | |
| 2004/0099213 A1 | 5/2004 | Adomaitis et al. | |
| 2004/0227087 A1 | 11/2004 | Markham et al. | |
| 2006/0056959 A1 * | 3/2006 | Sabol et al. | 415/118 |
| 2007/0227153 A1 * | 10/2007 | Truax | 60/772 |
| 2008/0016971 A1 * | 1/2008 | Bunce et al. | 73/865.5 |
| 2008/0238446 A1 * | 10/2008 | DeNatale et al. | 324/663 |

* cited by examiner

Primary Examiner—Eric S McCall

(57) ABSTRACT

Aspects of the invention are directed to the use of microelectromechanical systems (MEMS) based emissions sensors in a turbine engine system to measure one or more emissions values associated with a gas flow in the system. The emissions value can be, for example, the temperature of a gas flow and/or the amount of a particular compound, such as carbon monoxide, in the gas flow. Due to their small size, a plurality of MEMS emissions sensors can readily be incorporated at various locations in a turbine engine system. For example, the MEMS emissions sensors can be operatively positioned in an exhaust stack, downstream of the last row of blades in the turbine section, or in the leading edge of a turbine vane. The MEMS sensors can be operatively connected to a data acquisition system, which can statistically analyze the emissions values measured by the MEMS sensors.

20 Claims, 4 Drawing Sheets

MEMS EMISSIONS SENSOR SYSTEM FOR A TURBINE ENGINE

FIELD OF THE INVENTION

The invention relates in general to turbine engines and, more particularly, to a system for measuring emissions in a turbine engine.

BACKGROUND OF THE INVENTION

The combustion of fossil fuels in a gas turbine engine, such as in the context of a power generation plant, produces emissions that give rise to environmental concerns. Examples of emissions that are of concern include carbon monoxide (CO) and nitrogen oxides (NOx). Government regulations make the measurement of these and other compounds an operational requirement.

Current emissions sensor systems that are in compliance with Environmental Protection Agency (EPA) protocol are large, bulky and expensive. These systems include a sampling tube inside the exhaust stack of the power plant. The sampling tube is operatively connected to emissions measurement instruments located outside of the exhaust stack. In order to ensure their accurate performance, these instruments require regular calibration. Moreover, experience has revealed that the EPA protocol systems are repeatedly in need of repair. Such frequent calibration and repair of EPA protocol sensor systems appreciably adds to the cost of power plant operation. Thus, there is a need for an emissions sensor system that can minimize such concerns.

SUMMARY OF THE INVENTION

In one respect, aspects of the invention are directed to an emissions measurement system. The system includes a turbine engine and a gas flow in the turbine engine. The turbine engine can includes a row of rotating blades and a row of stationary vanes. Each vane can have an associated leading edge.

According to aspects of the invention, a plurality of MEMS emissions sensors are operatively positioned within the turbine engine. In one embodiment, the MEMS emissions sensors can be operatively positioned proximate the row of rotating blades. In another embodiment, the MEMS emissions sensors can be attached to one or more of the stationary vanes proximate the leading edge.

Each of the MEMS emissions sensors measures an emissions value of the gas flow. The emissions value can be the amount of carbon monoxide in the gas flow and/or the temperature of the gas flow. The MEMS emissions sensors can be adapted to withstand at least about 800 degrees Fahrenheit.

The system can further include a data acquisition system operatively connected to the plurality of MEMS emissions sensors. The data acquisition system can receive emissions values measured by the plurality of MEMS emissions sensors. The data acquisition system can be programmed with a statistical algorithm. Thus, the data acquisition system can statistically analyze the emissions values measured by the plurality of MEMS emissions sensors. Further, the data acquisition system is programmed to filter the emissions values based on at least one filter criteria, whereby measured emission values outside of the filter criteria are disregarded.

In another respect, an emissions measurement system according to aspects of the invention includes a turbine engine and exhaust stack having a flow passage. The flow passage receives an exhaust gas from the turbine engine. A plurality of MEMS emissions sensors is operatively positioned within the flow passage. Each of the plurality of MEMS emissions sensors measures an emissions value of the turbine engine exhaust gas. The emissions value can be the amount of carbon monoxide in the exhaust gas and/or the temperature of the exhaust gas. The MEMS emissions sensors can be adapted to withstand at least about 800 degrees Fahrenheit. In one embodiment, there can be a maximum of about 100 MEMS emissions sensors in an area of about one square millimeter.

The system can also include a data acquisition system that is operatively connected to the plurality of MEMS emissions sensors. Thus, the data acquisition system can receive emissions values measured by the plurality of MEMS emissions sensors. The data acquisition system can be programmed with a statistical algorithm. The data acquisition system can statistically analyze the emissions values measured by the plurality of MEMS emissions sensors. The data acquisition system can be programmed to filter the emissions values based on one or more filter criteria. Measured emission values outside of the filter criteria can be disregarded.

In still another respect, aspects of the invention are directed to a method of measuring turbine engine emissions. This method involves operating a turbine engine system, which includes a gas traveling along a gas flow path. A plurality of MEMS emissions sensors is operatively positioned within the gas flow path. An emissions value of the gas flow is measured by each of the plurality of MEMS emissions sensors. The emissions value can be the amount of carbon monoxide in the gas and/or the temperature of the gas.

The method can further include the step of statistically analyzing the measured emissions values. In one embodiment, this step can include performing an average, root mean square, Student's T and/or Monte Carlo statistical analysis. Further, the measured emissions values can be filtered based on one or more filter criteria. Measured emissions values that fall outside of the one or more filter criteria can be disregarded. The filter criteria can be a reasonableness filter, an accuracy filter and/or a consistency filter.

DETAILED DESCRIPTION OF EMBODIMENT OF THE INVENTION

Figure 1:
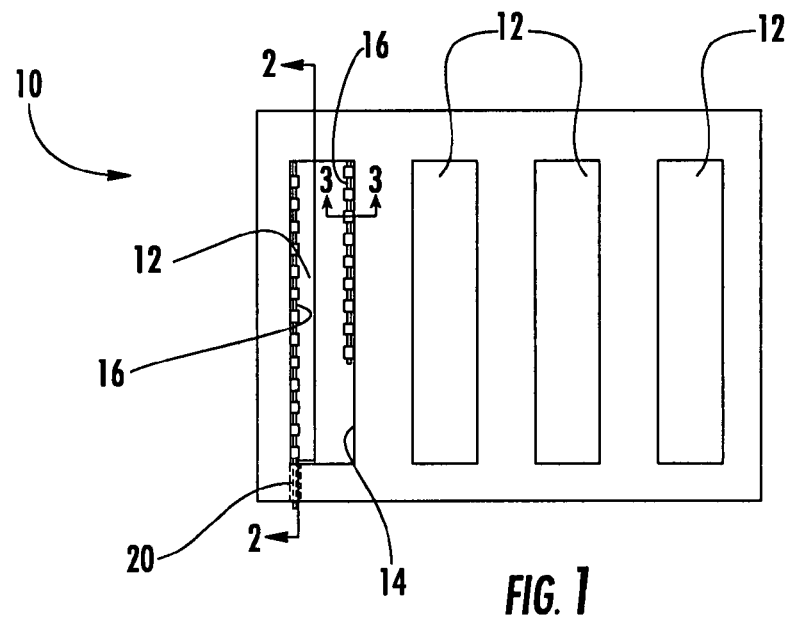
FIG. 1 is a top plan view of a turbine exhaust stack equipped with a plurality of MEMS emissions sensors according to aspects of the invention.

Embodiments of the invention are directed to a system for measuring various parameters associated with emissions produced during operation of a turbine engine. Aspects of the invention will be explained in connection with various possible systems, but the detailed description is intended only as exemplary. Embodiments of the invention are shown in FIGS. 1-9, but the present invention is not limited to the illustrated structure or application.

Microelectromechanical systems (MEMS) are a rapidly developing technology. MEMS are devices and machines that can be fabricated using techniques generally used in microelectronics, often to integrate mechanical functions with electrical functions. MEMS devices can be custom designed for a purpose which requires a mechanical action to be controlled by a computer.

Aspects of the invention are directed to the use of at least one MEMS-based emissions sensor at one or more locations in a turbine engine to measure one or more emissions values. Preferably, a plurality of MEMS emissions sensors are used because the flow in a turbine engine is typically not homogeneous. Due to their small size, the MEMS emissions sensors can readily be incorporated at various locations in a turbine engine with minimal disruption to the gas flow therein. A MEMS emissions sensor according to aspects of the invention can be adapted to operate in the high temperature environment of a turbine engine. The minimum temperature limit of the MEMS emissions sensors can vary from location-to-location. For instance, MEMS emissions sensors located in the exhaust stack of a turbine engine should be adapted to withstand at least about 800 degrees Fahrenheit. In other locations, such as the combustor section, the MEMS emissions sensors can be adapted to withstand even higher temperatures, such as about 3000 degrees Fahrenheit.

The MEMS emissions sensors according to aspects of the invention can measure any of a number of parameters associated with emissions produced during the operation of a turbine engine. In one embodiment, the MEMS emissions sensors can be adapted to measure the amount of carbon monoxide (CO) in a gas stream. However, the MEMS emissions sensors are not limited to the measurement of CO. Alternatively or in addition, the MEMS emissions sensors can be adapted to measure the amount of other compounds as well including, for example, oxygen, carbon dioxide and unburned hydrocarbons. The measurement of the amount of such compounds can be made in any suitable measurement unit, such as in parts per million. Another emissions parameter that can be measured by the MEMS emissions sensors is temperature. The MEMS emissions sensors can measure one or more emissions parameters on a continuous basis or at a plurality of discrete intervals on a regular or irregular basis.

The MEMS emissions sensors can have any suitable structure. In one embodiment, the MEMS emissions sensors can include a ceramic base, such as silicon oxide ($SiO_2$). On the base, there can be a plurality of conductors. These conductors can be made of any of a number of materials. For example, the conductors can be made of gold, platinum, titanium alloy, or any other material that is suited for the operational temperatures in a turbine engine. The conductors can be provided in a single layer or on multiple layers. An outer coating can be applied over the conductors. The outer coating can be a metal oxide film. The coating can be one that chemically reacts in the presence of a particular certain exhaust gas or at a certain temperature. Different coatings and different conductors can be used to verify the readings of the sensors.

The MEMS emissions sensors according to aspects of the invention can be provided in any of a number of forms. For instance, the MEMS emissions sensors can be provided as a plurality of individual sensors. Alternatively, the MEMS emissions sensors can be provided together as a group, such as in the form of a rope, cable, panel, plate, cluster or array, just to name a few possibilities. In one embodiment, the MEMS emissions sensors can be provided in a group of 16, such as in a 4×4 array. When provided as a group, each MEMS emissions sensor can be substantially adjacent to at least one other MEMS emissions sensor. The group of MEMS emissions sensors can form a single sensing unit, which can be used in place of the existing EPA protocol emissions sensor systems or thermocouples. Due to their small size, tens if not hundreds of MEMS emissions sensors can occupy the same space taken by these prior measurement devices.

The MEMS emissions sensors can be any suitable size or shape. For instance, the MEMS emissions sensors can be substantially circular or rectangular in cross-section. In one embodiment, a MEMS emissions sensor in accordance with aspects of the invention can have a cross-sectional area of no more than about 0.01 square millimeters to about 0.15 square millimeters. In one embodiment, each MEMS emissions sensor can have a substantially square cross-sectional shape. In such case, the length of each side can be from about 100 micrometers to about 300 micrometers.

For a given location, any suitable number of MEMS emissions sensors can be used so long as sufficient statistical accuracy can be achieved. Ideally, a single MEMS emissions sensor is used. For a given area, there can be any suitable density of MEMS emissions sensors. For instance, in an area of about 10 square millimeters, there can be a maximum of about 1000 MEMS emissions sensors. In one embodiment, there can be a maximum of about 10 to about 1000 MEMS emissions sensors in an area of about 10 square millimeters, depending on the size of the individual sensors. According to aspects of the invention, there can be from about 1 to about 100 MEMS emissions sensors per square millimeter.

The MEMS emissions sensors can be powered in any suitable manner. The power source can be external or internal to the engine. In one embodiment, the power source can be located on the same base as the conductors. The MEMS emissions sensors can be powered by any other suitable on-board device that generates electricity, which can be subsequently amplified. For example, the MEMS emissions sensors can be powered by an on-board thermopile, which can generate electrical energy from thermal energy using the Seebeck Effect. The thermopile can include a plurality of thermocouples arranged in any suitable manner. For instance, the thermocouples can be arranged in the form of a rosette. Alternatively or in addition, the MEMS emissions sensors can be self generating using a technique such as the Seebeck Effect or using modulating transducers that can rely on the Hall Effect for transmitting power and signal. In one embodiment, a magnet can be used to energize a transmitter, which can be used to transmit signal.

Figure 2:
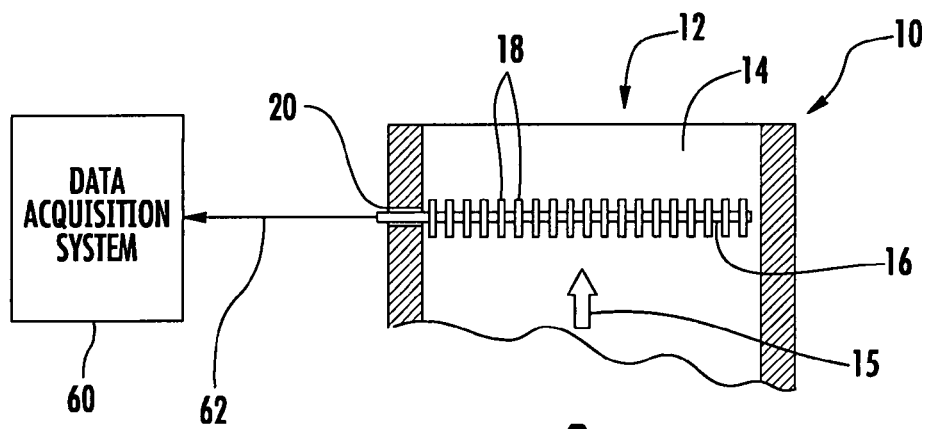
FIG. 2 is a cross-sectional view of a portion of the turbine exhaust stack, viewed from line 2-2 in FIG. 1.
Figure 3:
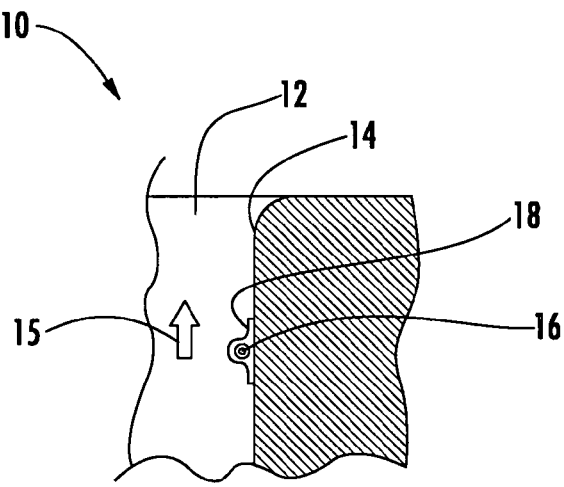
FIG. 3 is a cross-sectional view of a portion of the turbine exhaust stack, viewed from line 3-3 in FIG. 1.

As noted earlier, the MEMS emissions sensors can be used at various locations in a turbine engine system. For instance, the MEMS emissions sensors can be used to measure one or more emissions parameters associated with a discharge flow exiting an exhaust stack. FIGS. 1-3 show one embodiment of an exhaust stack 10 according to aspects of the invention.

Referring to FIG. 1, the turbine exhaust stack 10 can include a plurality of flow passages 12 therein. Each flow passage 12 can be defined by at least one wall 14. The flow passage 12 can contain a gas flow, which can be turbine exhaust gases 15 (FIG. 2).

According to aspects of the invention, a plurality of MEMS emissions sensors 16 can be operatively positioned within the flow passage 12. In one embodiment, the MEMS emissions sensors 16 can be attached to one of the walls 14 of the flow passage 12. In such case, the MEMS emissions sensors 16 can extend along at least a portion of the wall 14. Attachment of the MEMS emissions sensors 16 to the wall 14 can be achieved in various ways. FIGS. 2-3 show one manner of effecting such attachment. As shown, the plurality of MEMS emissions sensors 16 can be provided on an elongated flexible substrate, such as in a rope like form. The MEMS emissions sensors 16 can be attached to the wall by a plurality of retaining straps 18 that are attached to the wall 14 by, for example, welding, brazing or fasteners, just to name a few possibilities. A passage 20 (FIG. 3) can be provided in the wall 14 of the exhaust stack 10 to permit insertion and removal of the MEMS emissions sensors 16 from the exterior of the exhaust stack 10.

The plurality of MEMS emissions sensors 16 can be arranged in various ways. For instance, the MEMS emissions sensors 16 can be oriented substantially horizontally, substantially vertically, any orientation therebetween or any combination thereof. The MEMS emissions sensors 16 can be provided in a substantially linear arrangement, such as in one or more rows and/or one or more columns. However, the MEMS emissions sensors 16 can be provided in any of a number of non-linear arrangements as well. In instances where the plurality of MEMS emissions sensors 16 are provided in two or more separate groups, the sensor groups can be arranged in any of a number of ways relative to each other.

Figure 4:
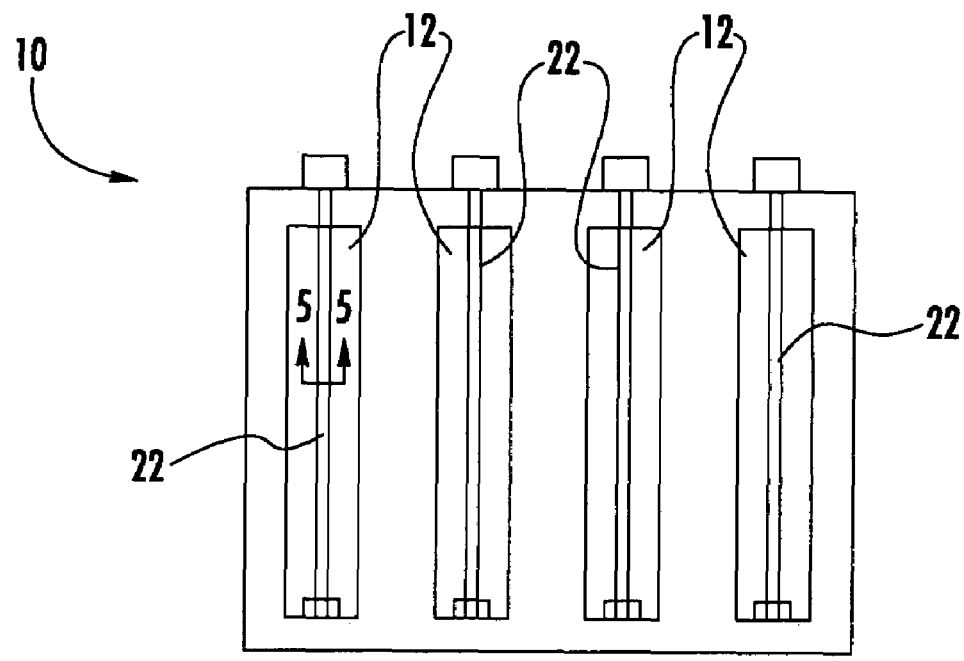
FIG. 4 is a top plan view of another turbine exhaust stack instrumented with MEMS emissions sensors according to aspects of the invention.
Figure 5:
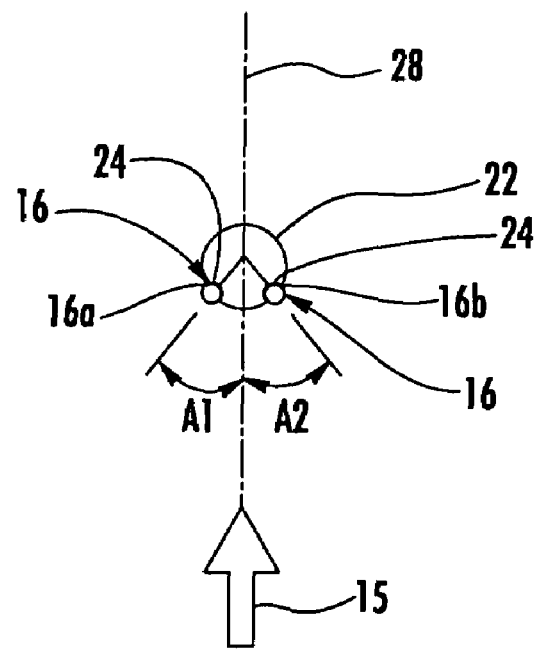
FIG. 5 is a cross-sectional view of a temperature measurement device, viewed from line 5-5 in FIG. 4 and showing a plurality of MEMS emissions sensors provided on the temperature measurement device.

In some exhaust systems, there can be additional components or hardware in the exhaust stack to which the MEMS emissions sensors 16 can be attached. Ideally, the MEMS emissions sensors 16 are arranged so that they do not interfere with the functioning of the component to which they are attached. FIG. 4 shows an example of an exhaust stack 10 in which each of the flow passages 12 includes a measurement device extending through the flow passage 12. The measurement device can be a temperature measurement device 22, sometimes referred to as a temperature rake. According to aspects of the invention, a plurality of MEMS emissions sensors can be operatively positioned on the temperature measurement device 22. FIG. 5 shows an example of a plurality of MEMS emissions sensors 16 operatively positioned on the temperature measurement device 22. In such case, the plurality of MEMS emissions sensors can be received within a recess 24 in the temperature measurement device 22, and they can be held therein by any suitable manner. The plurality of MEMS emissions sensors 16 can extend along at least a portion of the length of the temperature measurement device 22.

The plurality of MEMS emissions sensors 16 can be positioned at or proximate a portion of the temperature measurement device 22 that faces the exhaust flow 15. In one embodiment, as shown in FIG. 5, a first group of MEMS emissions sensors 16a can be oriented at a first angle A1 relative to the axis 28 of the flow passage 12. Likewise, a second group of MEMS emissions sensors 16b can be oriented at a second angle A2 relative to the axis 28 of the flow passage 12. The first and second angles A1, A2 may or may not be equal to each other. In one embodiment, the first and second angles A1, A2 can be about 30 degrees.

In another embodiment, the plurality of MEMS emissions sensors 16 can be provided on an elongated flexible substrate, such as in rope-like form. In such case, the MEMS emissions sensors 16 can be attached at one end to the temperature measurement device 22 and hang therefrom into the flow passage 12. In yet another embodiment, the plurality of MEMS emissions sensors 16 in rope-like form can be wrapped around at least a portion of the outer surface of the temperature measurement device 22.

In each of the above embodiments, the MEMS emissions sensors 16 can measure a desired emissions value based on exposure to the exhaust flow 15 in the stack 10. For example, the MEMS emissions sensors 16 can be adapted to measure carbon monoxide and/or temperature. Such emissions values can be used to determine whether any corrective action or maintenance is needed. For example, exhaust temperature can be used to control the turbine so as to keep the turbine inlet temperature substantially uniform.

Figure 6:
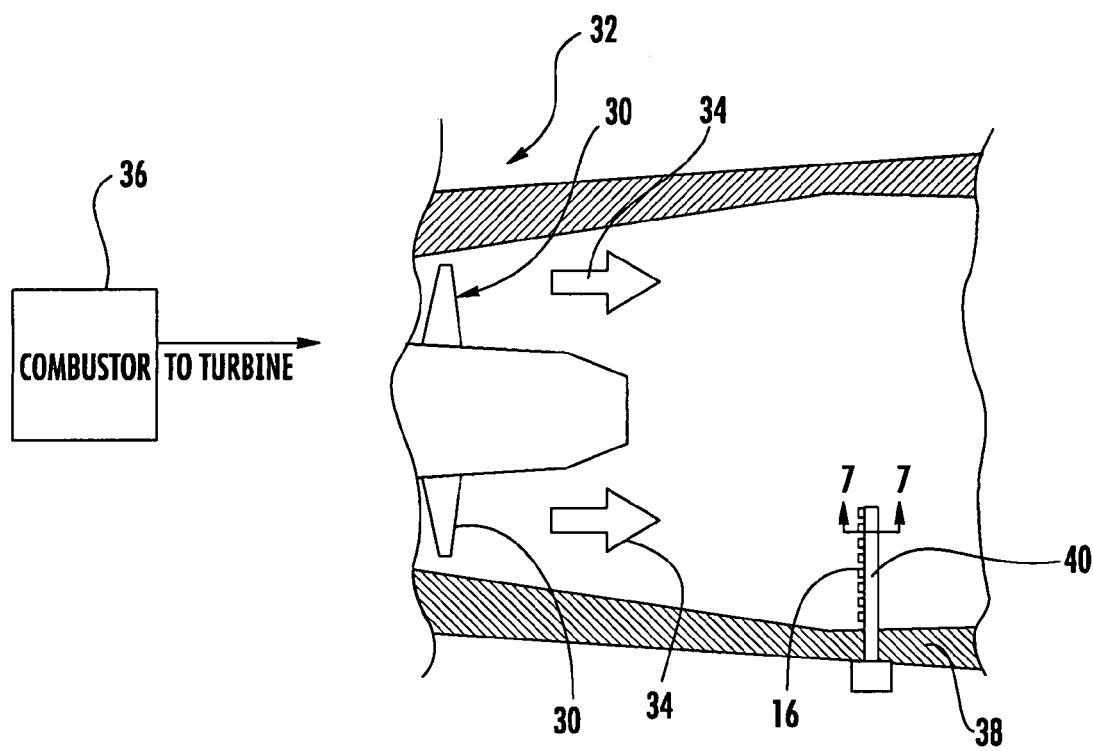
FIG. 6 is a cross-sectional view of a portion of the turbine exhaust that is equipped with MEMS emissions sensors according to aspects of the invention.

The foregoing embodiment of the turbine exhaust stack is just one of many areas in a turbine engine system in which the MEMS emissions sensors can be used. In another embodiment, the MEMS emissions sensors according to aspects of the invention can also be used to measure the emissions associated with an individual combustor of a turbine engine, such as an individual can-annular combustor. To that end, a plurality of MEMS emissions sensors 16 can be operatively positioned downstream of the last row of blades 30 in the turbine section 32, as shown in FIG. 6. Emissions values measured by the plurality of MEMS emissions sensors 16 can be used to identify poorly performing combustors. As is known, a portion of the flow 34 exiting the turbine section can be reliably correlated with a particular combustor 36 (only one of which is graphically represented in FIG. 6). That is, for a particular circumferential location (clock position), the gases 34 exiting the last row of blades 30 in the turbine section 32 can be traced back to a specific combustor 36 using, for example, analytical and/or experimental data or other known techniques. Such methods can be used to associate the emissions values measured by the plurality of MEMS emissions sensors 16 to a specific combustor 36.

The plurality of MEMS emissions sensors 16 can be placed in any suitable location to operatively engage the gases 34 exiting the turbine section 32. In one embodiment, the MEMS emissions sensors 16 can be attached to a turbine exhaust casing 38 downstream of the last row of blades 30. Alternatively, the MEMS emissions sensors 16 can be provided on any stationary structure in the area. For example, the MEMS emissions sensors 16 can be mounted on a temperature measurement device 40 positioned downstream of the last row of turbine blades 30. Typically, a plurality of temperature measurement devices 40 can be circumferentially arrayed about the turbine exhaust casing 38. Likewise, groups of the MEMS emissions sensors 16 can be circumferentially arrayed about the turbine exhaust casing.

Figure 7:
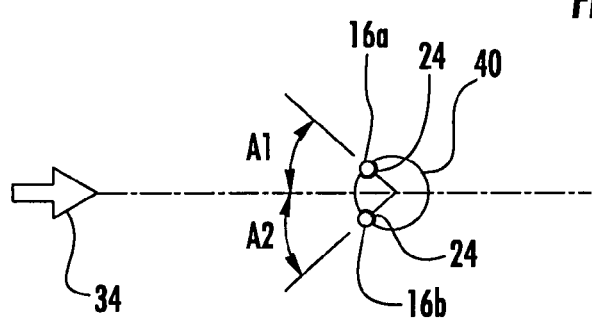
FIG. 7 is a cross-sectional view of a temperature measurement device, viewed from line 7-7 in FIG. 6, and showing a plurality of MEMS emissions sensors provided on the temperature measurement device.

In one embodiment, such as shown in FIG. 7, the MEMS emissions sensors 16 can be mounted proximate a portion of the temperature measurement device 40 that faces the oncoming flow 34 exiting the turbine section 32. The above discussion relating to the MEMS emissions sensors 16 on the temperature measurement device 22 in the exhaust stack 10 has equal application here.

Thus, the plurality of MEMS emissions sensors 16 can measure one or more emissions values. In one embodiment, the MEMS emissions sensors 16 can measure CO. With the measured CO values, individual combustors 36 that are producing excessive CO emissions or otherwise performing and/or functioning poorly can be identified so that remedial action can be taken.

Figure 8:
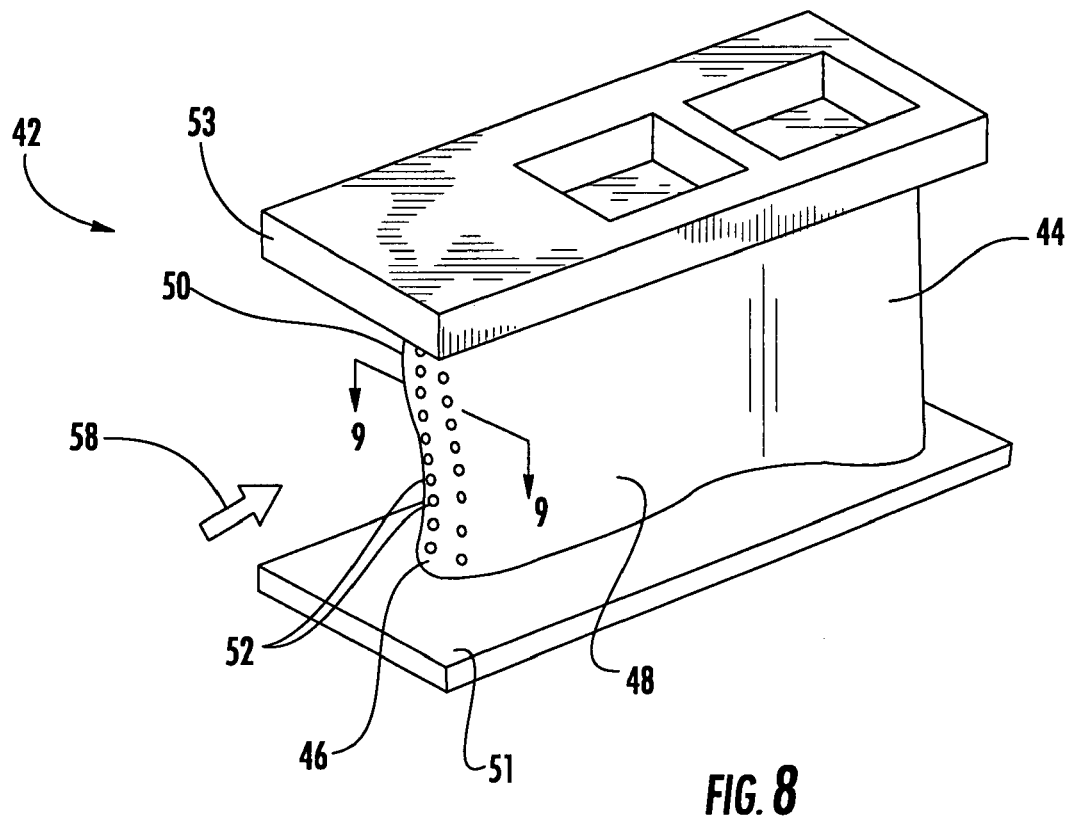
FIG. 8 is an isometric view of a turbine vane equipped with a plurality of emissions sensors according to aspects of the invention.
Figure 9:
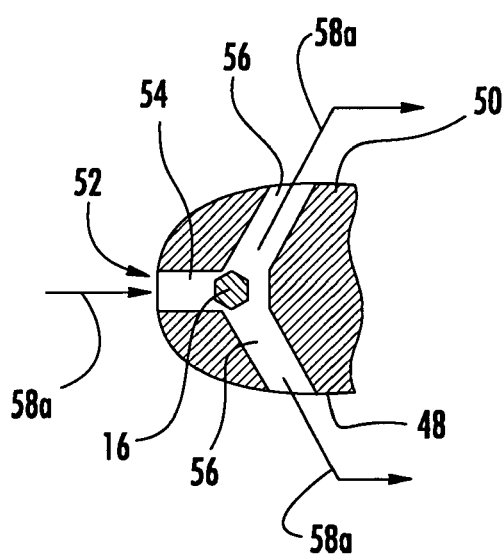
FIG. 9 is a cross-sectional view of a portion of the vane, viewed from line 9-9 in FIG. 8, and showing one possible arrangement of the MEMS emissions sensors proximate the leading edge of the vane.

In another embodiment, one or more emissions values associated with the flow exiting a combustor 36 can be obtained by operatively positioning a plurality of MEMS sensors 16 on a turbine vane. FIGS. 8-9 show one example of such an arrangement. As shown, a turbine vane 42 includes an airfoil portion 44 having a leading edge 46, a pressure side 48 and a suction side 50. In addition, the vane 42 includes an inner shroud 51 and an outer shroud 53.

The MEMS emissions sensors 16 can be attached to the vane 42 in any of a number of ways. According to aspects of the invention, a plurality of MEMS sensors 16 can be positioned at or proximate the leading edge 46 of the turbine vane 42. For instance, a plurality of sampling passages 52 can be formed in the turbine vane, such as by casting or machining. Each sampling passage 52 can include an inlet passage 54 and at least one discharge passage 56. In one embodiment, the sampling passage 52 can include one inlet passage 54 and two discharge passages 56 branching therefrom, as shown in FIG. 9. One of the discharge passages 56 can open to the suction side 50 of the airfoil 44, and the other discharge passage 56 can open to the pressure side 48 of the airfoil 44. At least one MEMS emissions sensor 16 can be placed along the sampling passage 52 so as not to restrict the flow. In one embodiment, the MEMS emissions sensors 16 can be placed proximate the transition between the inlet passage 54 and the discharge passage 56.

During engine operation, a portion of the combustion gases 58a can enter the sampling passage 54 and operatively engage the MEMS emissions sensors 16, which can measure one or more emissions values of the portion of combustion gases 58. After engaging the sensors 16, the gases 58a can exit through the at least one discharge passage 56 to rejoin the rest of the hot gases 58 in the turbine.

In each of the above systems, the plurality of MEMS emissions sensors 16 can be operatively connected to a data acquisition system 60 (see, for example, FIG. 2). The data acquisition system 60 can be, for example, a microprocessor, a computer or other system that can acquire, store, process and/or analyze or process data. The data acquisition system 60 can be a single component or a plurality of separate components that are operatively connected.

In one embodiment, the MEMS emissions sensors 16 can be operatively connected to the data acquisition system 60 by one or more conductors 62. Alternatively, there can be wireless transmission of data between the MEMS emissions sensors 16 and the data acquisition system 60. However, aspects of the invention are not limited to any particular manner of operatively connecting the MEMS emissions sensors 16 and the data acquisition system 60. The operative connection between the MEMS emissions sensors 16 and the data acquisition system 60 can permit unidirectional or bidirectional communication therebetween.

In the case of a single MEMS emissions sensor, the emissions value measured by the MEMS emissions sensor is the only reading. Subsequent action can be taken, if necessary, based on this single reading. As emission values from the single MEMS emissions are recorded over time, one emissions value can be compared to preceding and/or subsequent emissions values measured by the MEMS emission sensor. The data acquisition system can be programmed to analyze historical trends and consistency in the readings.

In the case of a plurality of sensors, the emissions values obtained by the MEMS emissions sensors 16 can be statistically analyzed. To that end, the data acquisition system 60 can be programmed to perform at least one statistical analysis on the emissions values, such as by using a statistical analysis algorithm or software. Any suitable statistical analysis can be used. For example, the data acquisition system 60 can compute the average emissions value measured by the plurality of sensors 16 at a given location and/or at a given time. Further, the plurality of emissions values can be statistically analyzed using a "Student's T," a "Monte Carlo" and/or a "Root Mean Square" analysis. Again, these are just a few examples of various known statistical tools that can be used to analyze the emissions values obtained by the plurality of MEMS emissions sensors 16.

The accuracy of the MEMS emissions sensors can be increased by filtering the emissions values measured by the MEMS emissions sensors. The emissions values can be filtered by any suitable method and according to any suitable filter criteria. Emissions values that do not pass the filter criteria can be disregarded or discarded. As a result of such filtering, higher levels of statistical confidence can be achieved when performing statistical analyses with the remaining measured emissions values.

One manner of filtering the data is described below. It will be understood that the filtering method described is provided merely as an example and is not intended to limit the scope of the invention to any particular filtering method or filter criteria. In each case, the filter criteria may or may not be predetermined.

In one embodiment, the measured emissions values can be filtered based on a reasonableness criteria. The reasonableness criteria can be set to identify emissions values that would be impossible or, at a minimum, highly unlikely. Thus, any measured emissions values falling outside of the reasonableness criteria can be eliminated from the sample of emissions values.

For example, there are carbon monoxide emissions values that can be present in a diffused or premixed flame in a gas turbine engine, and there are those carbon monoxide emissions values that would not be possible during engine operation. Thus, if a MEMS CO sensor is measuring a CO emissions value that cannot be present during engine operation when the engine is in operation, then that CO emissions value can be eliminated from the data set.

Alternatively or in addition to the reasonableness criteria, an accuracy criteria can be applied to filter the measured emissions values. An individual emissions value measured by one of the MEMS emissions sensors should be substantially consistent with the preceding and subsequent measurements on that same MEMS emissions sensor, particularly when the measurements are made close in time. Further, the emissions value measured by one MEMS emissions sensor should also be about the same as emissions values measured by nearby MEMS emissions sensors at substantially the same time. Measured emissions values that are significantly different from emissions values measured by the same MEMS emissions sensor or by a nearby MEMS emissions sensor can be labeled as suspect, if not disregarded altogether.

The accuracy criteria can be based on other factors, at least in part, to account for some changes in the measured emissions values over time. For example, the accuracy criteria can take into account the gas velocity and/or type of combustion. With such information, an expected rate of change of the amount of CO in the exhaust can be determined to account for changes in the measured emissions values.

The accuracy criteria can be useful in embodiments where individual emissions values are averaged before being passed on for statistical analysis. For instance, emissions values can be averaged over a ten second interval with the emissions values being measured every second. Eight of the ten emissions values can be, for example, 10 units, and two of the ten emissions values can be, for example, 100 units. In such case, the overall average of the ten emissions values is 28. It could be assumed that the two measurements of 100 units are bad data, but that assumption could be wrong. It cannot be assumed that there is more good data than bad data. If the previous average was 10 and the following average is 100, then perhaps the average of 28 is correct or, at a minimum, it cannot be labeled as incorrect. However, if the previous average was 100 and the following average is 100, then perhaps the average of 28 indicates that there were more wrong measurements than right measurements in the data sample, so the data should be considered unreliable.

Alternatively or in addition to the reasonableness criteria and/or the accuracy criteria, the data can be filtered according to a consistency criteria. The consistency criteria is intended to make sure that the emissions values being measured should be considered valid. Each particular MEMS emissions sensor being used has an expected uncertainty. If there is a series of measured emissions values from one MEMS emissions sensor that is more (such as, from about 10 to about 30 percent more) than the expected uncertainty of that individual MEMS emissions sensor, as compared to the nearby MEMS emissions sensors, then there is a consistency problem and the measurements from that one MEMS emissions sensor can be discarded or otherwise ignored. In cases where the MEMS emissions sensors are inconsistent among themselves, further investigation is warranted before statistical analyses are applied to such data.

It should be noted that the above filters are merely examples. Any quantity and combination of filters can be applied. Further, there may be overlap between the different filters. The emissions values can be filtered before they are submitted for statistical analysis. The filtered emissions values can make up a statistically significant set of emissions values for analysis. In addition to achieving better data for analysis, filtering the MEMS emissions values can be used to account for the inevitable degradation and failure of individual MEMS emissions sensors over time. The data acquisition system 60 can be programmed to generate a confidence matrix to determine when individual MEMS emissions sensors 16 or entire sensor arrays or groups require replacement.

The MEMS emissions sensors systems according to aspects of the invention can provide an inexpensive, accurate method of measuring emissions values in a gas turbine. Ideally, the system according to aspects of the invention can replace the known EPA protocol sensor systems and minimize the drawbacks associated therewith. For instance, unlike current EPA protocol sensor systems, periodic calibration of the MEMS emissions sensors would not be necessary. The MEMS emissions sensors will either work, or they will not work. Thus, only functional checks will be required. Sensing accuracy and calibration problems can be overcome by installing arrays of these sensors and using statistical techniques to increase overall accuracy and stability.

The foregoing description is provided in the context of various possible applications for a MEMS-based emissions sensor system in a turbine engine system. Aspects of the invention are not intended to be limited to the foregoing examples. Thus, it will of course be understood that the invention is not limited to the specific details described herein, which are given by way of example only, and that various modifications and alterations are possible within the scope of the invention as defined in the following claims.

What is claimed is:

1. An emissions measurement system comprising:
   a turbine engine;
   a gas flow in the turbine engine;
   a plurality of MEMS emissions sensors operatively positioned within the turbine engine, the plurality of MEMS emissions sensors being grouped together such that each MEMS emissions sensor is substantially adjacent to at least one other MEMS emissions sensor, wherein each of the MEMS emissions sensors measures an emissions value of the gas flow; and
   a data acquisition system operatively connected to the plurality of MEMS emissions sensors, wherein the data acquisition system receives emissions values measured by the plurality of MEMS emissions sensors, the data acquisition system being programmed with a statistical algorithm such that the data acquisition system statistically analyzes the emissions values measured by the plurality of MEMS emissions sensors.

2. The system of claim 1 wherein the emissions value is at least one of the amount of carbon monoxide in the gas flow or the temperature of the gas flow.

3. The system of claim 1 wherein the MEMS emissions sensors are adapted to withstand at least about 800 degrees Fahrenheit.

4. The system of claim 1 wherein the turbine engine includes a row of rotating blades, wherein the plurality of MEMS emissions sensors are operatively positioned proximate the row of rotating blades.

5. The system of claim 1 wherein the turbine engine includes a row of stationary vanes, each vane having a leading edge, wherein the plurality of MEMS emissions sensors are attached to at least one of the stationary vanes proximate the leading edge.

6. The system of claim 1 wherein the data acquisition system is programmed to filter the emissions values based on at least one filter criteria, whereby measured emission values outside of the filter criteria are disregarded.

7. The system of claim 1 wherein the plurality of MEMS emissions sensors are provided in an area of about one square millimeter.

8. The system of claim 1 wherein the filter criteria is at least one of a reasonableness filter, an accuracy filter or a consistency filter.

9. The system of claim 1 wherein the statistical algorithm is configured to perform at least one of the following statistical analyses: average, root mean square, Student's T or Monte Carlo.

10. An emissions measurement system comprising:
    a turbine engine;
    an exhaust stack having a flow passage, wherein the flow passage receives an exhaust gas from the turbine engine;
    a plurality of MEMS emissions sensors operatively positioned within the flow passage, the plurality of MEMS emissions sensors being grouped together such that each MEMS emissions sensor is substantially adjacent to at least one other MEMS emissions sensor, wherein each of the plurality of MEMS emissions sensors measures an emissions value of the exhaust gas; and
    a data acquisition system operatively connected to the plurality of MEMS emissions sensors, wherein the data acquisition system receives emissions values measured by the plurality of MEMS emissions sensors, the data acquisition system being programmed with a statistical algorithm such that the data acquisition system statistically analyzes the emissions values measured by the plurality of MEMS emissions sensors.

11. The system of claim 10 wherein the emissions value is at least one of the amount of carbon monoxide in the exhaust gas or the temperature of the exhaust gas.

12. The system of claim 10 wherein the plurality of MEMS emissions sensors are provided in an area of about one square millimeter.

13. The system of claim 10 wherein the statistical algorithm is configured to perform at least one of the following statistical analyses: average, root mean square, Student's T or Monte Carlo.

14. The system of claim 10 wherein the data acquisition system is programmed to filter the emissions values based on at least one filter criteria, whereby measured emission values outside of the filter criteria are disregarded.

15. The system of claim 14 wherein the filter criteria is at least one of a reasonableness filter, an accuracy filter or a consistency filter.

16. A method of measuring turbine engine emissions comprising the steps of:
 operating a turbine engine system, wherein the turbine engine system includes a gas traveling along a gas flow path;
 operatively positioning a plurality of MEMS emissions sensors within the gas flow path;
 measuring an emissions value of the gas flow with each of the plurality of MEMS emissions sensors;
 filtering the measured emissions values based on at least one filter criteria such that measured emissions values outside of the at least one filter criteria are disregarded; and
 statistically analyzing the filtered measured emissions values.

17. The method of claim 16 wherein the statistically analyzing step includes performing at least one of the following statistical analyses: average, root mean square, Student's T or Monte Carlo.

18. The method of claim 16 wherein the filter criteria is at least one of a reasonableness filter, an accuracy filter or a consistency filter.

19. The method of claim 16 wherein the emissions value is at least one of the amount of carbon monoxide in the gas or the temperature of the gas.

20. The method of claim 16 wherein the plurality of MEMS emissions sensors are grouped together such that each MEMS emissions sensor is substantially adjacent to at least one other MEMS emissions sensor.

* * * * *